(12) United States Patent
Okano (10) Patent No.: US 9,019,098 B2
(45) Date of Patent: Apr. 28, 2015

(54) WIRELESS COMMUNICATION SYSTEM

(75) Inventor: Hideo Okano, Hanno (JP)

(73) Assignee: Olympus Corporation, Tokyo (JP)

(*) Notice: Subject to any disclaimer, the term of this patent is extended or adjusted under 35 U.S.C. 154(b) by 38 days.

(21) Appl. No.: 13/489,087

(22) Filed: Jun. 5, 2012

(65) Prior Publication Data

US 2012/0313760 A1   Dec. 13, 2012

(30) Foreign Application Priority Data

Jun. 7, 2011   (JP) ................................ 2011-127553

(51) Int. Cl.
   *G08B 1/08*   (2006.01)
   *G06F 19/00*   (2011.01)
   *G06Q 50/22*   (2012.01)

(52) U.S. Cl.
   CPC ............ *G06F 19/3418* (2013.01); *G06Q 50/22* (2013.01)
   USPC .................................................. 340/539.12

(58) Field of Classification Search
   CPC .................................................. G06K 7/0008
   USPC ......... 340/10.1, 573.1, 539.12; 600/300, 301; 705/2, 3; 370/311
   See application file for complete search history.

(56) References Cited

U.S. PATENT DOCUMENTS

| | | | |
|---|---|---|---|
| 5,924,979 A * | 7/1999 | Swedlow et al. | 600/300 |
| 6,200,265 B1 * | 3/2001 | Walsh et al. | 600/300 |
| 7,957,813 B1 * | 6/2011 | Persson et al. | 607/60 |
| 2004/0006492 A1 * | 1/2004 | Watanabe | 705/2 |
| 2008/0318624 A1 * | 12/2008 | Hedtke et al. | 455/556.1 |
| 2009/0264964 A1 * | 10/2009 | Abrahamson | 607/60 |

FOREIGN PATENT DOCUMENTS

| | | |
|---|---|---|
| JP | 11-128174 A | 5/1999 |
| JP | 2002-102362 A | 4/2002 |
| JP | 2002-163742 A | 6/2002 |
| JP | 2004-129905 A | 4/2004 |
| JP | 2005-286655 A | 10/2005 |
| JP | 2006-187316 A | 7/2006 |
| JP | 2008-061663 A | 3/2008 |
| JP | 2008-119479 A | 5/2008 |
| JP | 2008-178626 A | 8/2008 |
| JP | 2009-247812 A | 10/2009 |
| WO | WO 2011034468 A1 * | 3/2011 ............. A61N 1/372 |

OTHER PUBLICATIONS

Office Action dated Feb. 24, 2015, issued in corresponding Japanese Patent Application No. 2011-127553, with English translation (6 pages).

* cited by examiner

*Primary Examiner* — Hai Phan
*Assistant Examiner* — Zhen Y Wu
(74) *Attorney, Agent, or Firm* — Westerman, Hattori, Daniels & Adrian, LLP (57) ABSTRACT

A wireless communication system may include a wireless communication unit configured to wirelessly receive vital data from a sensing terminal, a storage unit configured to store comparison vital data, a comparison unit configured to compare the wirelessly received vital data with the comparison vital data, and a control unit configured to control the wireless communication unit to transmit an instruction for stopping wireless transmission of the vital data to the sensing terminal that has wirelessly transmitted the vital data based on a comparison result of the comparison unit.

7 Claims, 7 Drawing Sheets

WIRELESS COMMUNICATION SYSTEM

BACKGROUND OF THE INVENTION

1. Field of the Invention

The present invention relates to a wireless communication system.

Priority is claimed on Japanese Patent Application No. 2011-127553, filed Jun. 7, 2011, the content of which is incorporated herein by reference.

2. Description of the Related Art

All patents, patent applications, patent publications, scientific articles, and the like, which will hereinafter be cited or identified in the present application, will hereby be incorporated by reference in their entirety in order to describe more fully the state of the art to which the present invention pertains.

In the medical and health care fields, there has been an increased effort to collect biological data from the surface of a human body or the inside of the body using a terminal provided with various sensors, transmit the biological data collected by the terminal to a storage device for storage, and use the biological data stored in the storage device for health management, disease diagnosis, medical treatment and the like (for example, refer to Japanese Unexamined Patent Application, First Publication No. 2002-102362). For this purpose, if the terminal is connected to the storage device using a wired cable in order to transmit the biological data, since the freedom of movement is limited, it is preferable to transmit the biological data through wireless communication, and to drive the terminal using a battery such that a user can freely carry the terminal. These needs are significantly increased in the medical field, particularly, for an implantable medical device (IMD).

Furthermore, the IMD generally operates with power from a battery. Accordingly, when the battery is exhausted and its voltage is reduced, battery exchange is required. Since the battery exchange of the IMD requires surgery, which causes a large burden to a patient and may generate adverse effects such as an infection, it is desirable to minimize the consumption of the battery.

Furthermore, in the IMD, when an emergency has occurred, a sensor generally detects emergency information, and a transfer destination or a transfer method of the emergency content is changed according to the level of emergency of the detected emergency information. Furthermore, after the sensor detects the emergency information, the IMD continuously transmits the biological data to the storage device. Furthermore, a radio meter inspection system for suppressing power consumption through intermittent driving has been disclosed (for example, refer to Japanese Unexamined Patent Application, First Publication No. 2005-286655).

SUMMARY

The present invention provides a wireless communication system capable of switching an operation mode of a sensing terminal to an operation mode with low power consumption.

A wireless communication system may include: a wireless communication unit configured to wirelessly receive vital data from a sensing terminal; a storage unit configured to store comparison vital data; a comparison unit configured to compare the wirelessly received vital data with the comparison vital data; and a control unit configured to control the wireless communication unit to transmit an instruction for stopping wireless transmission of the vital data to the sensing terminal that has wirelessly transmitted the vital data based on a comparison result of the comparison unit.

The storage unit may store heart rate data or blood sugar data as the comparison vital data.

The control unit may control the wireless communication unit to transmit the instruction based on the result obtained by comparing the wirelessly received vital data with the comparison vital data for a plurality of cycles.

When, comparing two of a plurality of sensing modes of the sensing terminal, a mode having a relatively long sensing interval is defined as a first mode and a mode having a relatively short sensing interval is defined as a second mode, the instruction may include an instruction for operating the sensing terminal in the first mode.

The wireless communication system may further include: an activation signal reception unit configured to receive an activation signal. When the activation signal reception unit receives the activation signal, the control unit may activate the wireless communication unit.

After the wireless communication unit receives the instruction, the control unit may stop an operation of the wireless communication unit.

A wireless communication system may include: a server; and a wireless communication terminal. The server may include: a communication unit configured to communicate with the wireless communication terminal; a storage unit configured to store comparison vital data; a comparison unit configured to compare vital data received from the wireless communication terminal with the comparison vital data; and a server control unit configured to control the communication unit to transmit a comparison result signal indicating a comparison result of the comparison unit to the wireless communication terminal. The wireless communication terminal may include: a first wireless communication unit configured to wirelessly receive the vital data from a sensing terminal; a second communication unit configured to transmit the vital data received from the sensing terminal to the server; and a control unit configured to control the first wireless communication unit to transmit an instruction for stopping wireless transmission of the vital data to the sensing terminal that has wirelessly transmitted the vital data based on the comparison result signal received from the server.

According to the present invention, the wireless communication unit wirelessly receives vital data from the sensing terminal. Furthermore, the storage unit stores comparison vital data. Furthermore, the comparison unit compares the wirelessly received vital data with the comparison vital data. Furthermore, based on the comparison result of the comparison unit, the control unit controls the wireless communication unit to transmit an instruction for stopping the wireless transmission of the vital data to the sensing terminal that has wirelessly transmitted the vital data. With such a configuration, based on the comparison result of the wirelessly received vital data and the comparison vital data, it is possible to stop the transmission of the vital data. Accordingly, it is possible to switch the operation mode of the sensing terminal to an operation mode with low power consumption.

BRIEF DESCRIPTION OF THE DRAWINGS

The above features and advantages of the present invention will be more apparent from the following description of certain preferred embodiments taken in conjunction with the accompanying drawings, in which.

DETAILED DESCRIPTION OF THE PREFERRED EMBODIMENTS

The present invention will be now described herein with reference to illustrative preferred embodiments. Those skilled in the art will recognize that many alternative preferred embodiments can be accomplished using the teaching of the present invention and that the present invention is not limited to the preferred embodiments illustrated for explanatory purpose.

Figure 1:
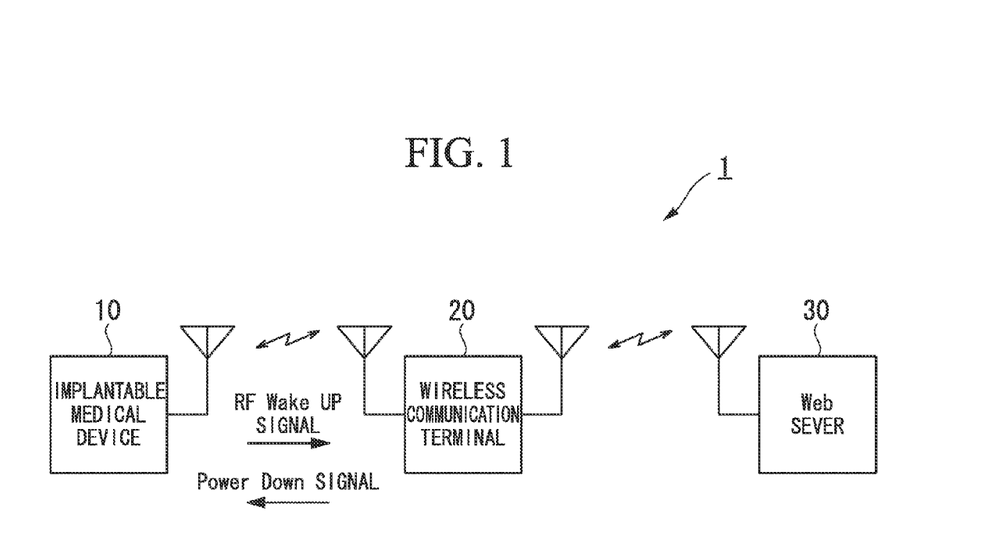
FIG. 1 is a schematic diagram illustrating a configuration of a biological data monitoring system in accordance with a first preferred embodiment of the present invention.

Hereinafter, a first preferred embodiment of the present invention will be described with reference to the accompanying drawings. FIG. 1 is a schematic diagram illustrating a configuration of a biological data monitoring system in accordance with the first preferred embodiment of the present invention. A biological data monitoring system 1 includes an implantable medical device (IMD) 10 (a sensing terminal), a wireless communication terminal 20, and a Web server 30. In the first preferred embodiment, the IMD 10 and the wireless communication terminal 20 wirelessly communicate with each other in a one-to-one manner. Furthermore, the wireless communication terminal 20 and the Web server 30 wirelessly communicate with each other in a one-to-one manner. In addition, communication between the wireless communication terminal 20 and the Web server 30 is not limited to wireless communication, and may include wired communication.

The IMD 10 is implanted inside of a human body to acquire biological data (vital data), such as blood pressure, pulse, electrocardiograph, heartbeat, blood oxygen level, body temperature, glycosuria, or blood sugar, or device status data, which indicates statuses of units provided in the IMD 10, using various sensors. In the first preferred embodiment, the biological data and the device status data will be referred to as detailed data.

Furthermore, the IMD 10 operates in one of two modes, that is, a normal mode (a first mode) and an emergency mode (a second mode). In the normal mode, the IMD 10, for example, acquires the detailed data once a day or once every 12 hours. Furthermore, in the normal mode, the IMD 10 does not transmit the detailed data to the wireless communication terminal 20. In the emergency mode, the IMD 10, for example, acquires the detailed data every five seconds. Furthermore, in the emergency mode, the IMD 10 transmits the detailed data to the wireless communication terminal 20.

Furthermore, based on the acquired detailed data, the IMD 10 performs an emergency level determination process of determining whether or not to change the operation mode of the IMD 10 from the normal mode to the emergency mode. When it is determined that the operation mode is changed from the normal mode to the emergency mode, the IMD 10 changes the operation mode to the emergency mode and performs a process corresponding to the emergency mode. In detail, the IMD 10 acquires the detailed data every 10 seconds. Furthermore, the IMD 10 transmits an RF Wake UP signal to the wireless communication terminal 20, and then transmits the detailed data to the wireless communication terminal 20, wherein the RF Wake UP signal activates a wireless interface of the wireless communication terminal 20.

Furthermore, when a measurement mode change signal serving as an instruction to change the operation mode of the IMD 10 from the emergency mode to the normal mode is received from the wireless communication terminal 20, the IMD 10 changes the operation mode from the emergency mode to the normal mode, and performs a process corresponding to the normal mode. In detail, the IMD 10 acquires the detailed data every minute. Furthermore, the IMD 10 stops the transmission of the detailed data to the wireless communication terminal 20. Furthermore, when a Power Down signal instructing to stop the operation of a wireless communication unit has been received from the wireless communication terminal 20, the IMD 10 stops the operation of the wireless communication unit.

When the RF Wake UP signal transmitted from the IMD 10 has been received, the wireless communication terminal 20 activates the wireless communication interface to prepare to receive the detailed data. Furthermore, after activating the wireless communication interface, the wireless communication terminal 20 receives the detailed data transmitted from the IMD 10, and stores the detailed data in a storage unit. Furthermore, the wireless communication terminal 20 transmits the detailed data received from the IMD 10 to the Web server 30.

Furthermore, the wireless communication terminal 20 receives a schematic determination signal from the Web server 30, wherein the schematic determination signal indicates a result obtained by determining whether or not to change the operation mode of the IMD 10 from the emergency mode to the normal mode. When the received schematic determination signal indicates that the operation mode of the IMD 10 is changed from the emergency mode to the normal mode, the wireless communication terminal 20 transmits a data measurement mode change signal to the IMD 10, wherein the data measurement mode change signal instructs a change from the emergency mode to the normal mode. Furthermore, when the received schematic determination signal indicates that the operation mode of the IMD 10 is changed from the emergency mode to the normal mode, the wireless communication terminal 20 transmits the Power Down signal to the IMD 10, wherein the Power Down signal instructs to stop the operation of the wireless communication unit of the IMD 10.

The Web server 30 performs a detailed determination process of determining whether or not to change the operation mode of the IMD 10 from the emergency mode to the normal mode based on the detailed data transmitted from the wireless communication terminal 20 and SDB information data blocks stored in advance. The detailed determination process will be described later. Then, the Web server 30 transmits a determination signal indicating a determination process result to the wireless communication terminal 20.

In addition, a wireless communication system according to the claims, for example, corresponds to the wireless communication terminal 20 or the Web server 30.

Figure 2:
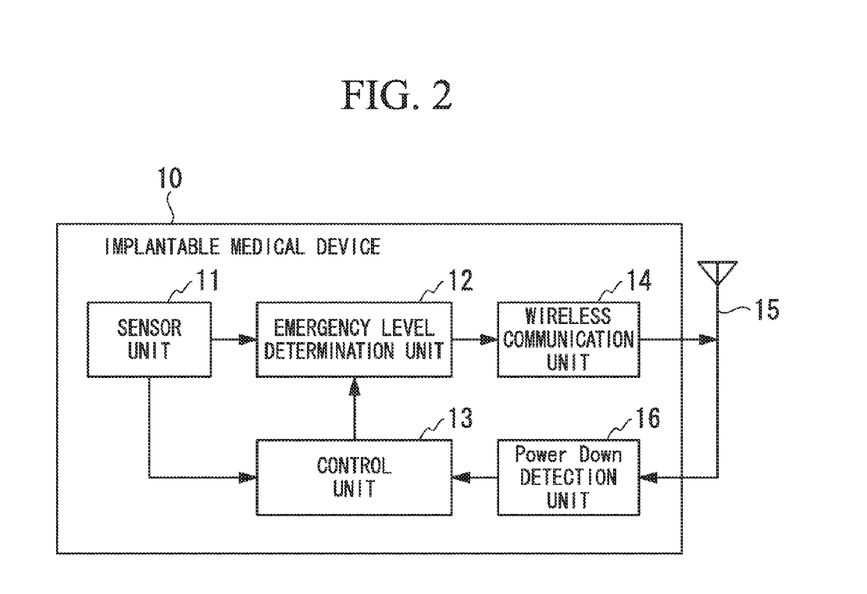
FIG. 2 is a block diagram illustrating the configuration of the IMD in accordance with the first preferred embodiment of the present invention.

Next, the configuration of the IMD 10 will be described. FIG. 2 is a block diagram illustrating the configuration of the IMD 10 in accordance with the first preferred embodiment of the present invention. In the example illustrated in FIG. 2, the IMD 10 includes a sensor unit 11, an emergency level determination unit 12, a control unit 13, a wireless communication unit 14, an antenna 15, and a Power Down detection unit 16.

The sensor unit 11 senses the biological data, such as blood pressure, pulse, electrocardiograph, heartbeat, a blood oxygen level, body temperature, glycosuria, or blood sugar, and outputs the biological data to the emergency level determination unit 12. Furthermore, the sensor unit 11 acquires the device status data by sensing the statuses of the units provided in the IMD 10, and outputs the device status data to the emergency level determination unit 12. In addition, the sensor unit 11 has a plurality of sensing modes, and sensing intervals are different from each other according to the operation mode of the IMD 10. In detail, when the operation mode of the IMD 10 is the normal mode, the sensor unit 11 acquires the detailed data every minute. Furthermore, when the operation mode of the IMD 10 is the emergency mode, the sensor unit 11 acquires the detailed data every 10 seconds.

When an event (abnormality of the biological data or abnormality of the device status data) has occurred, the emergency level determination unit 12 detects the event based on the detailed data input from the sensor unit 11. Furthermore, when the event has been detected, the emergency level determination unit 12 determines whether or not to change the operation mode of the IMD 10 from the normal mode to the emergency mode. For example, when the detected event is a mild event, the emergency level determination unit 12 determines that the operation mode of the IMD 10 is not changed to the emergency mode. When the detected event is a severe event, the emergency level determination unit 12 determines that the operation mode of the IMD 10 is changed to the emergency mode. Furthermore, when the IMD 10 operates in the emergency mode, the emergency level determination unit 12 outputs the detailed data input from the sensor unit 11 to the wireless communication unit 14.

The control unit 13 controls the units provided in the IMD 10 such that the IMD 10 performs an operation corresponding to the operation mode. In detail, when the emergency level determination unit 12 has determined that the operation mode is changed to the emergency mode, the control unit 13 changes the operation mode of the IMD 10 to the emergency mode, and activates the wireless communication unit 14. Then, the control unit 13 controls the wireless communication unit 14 to transmit the RF Wake UP signal to the wireless communication terminal 20. Furthermore, when the measurement mode change signal is received from the wireless communication terminal 20, the control unit 13 changes the operation mode of the IMD 10 from the emergency mode to the normal mode. Furthermore, when the Power Down signal has been input from the Power Down detection unit 16, the control unit 13 stops the operation of the wireless communication unit 14.

When the IMD 10 operates in the emergency mode, the wireless communication unit 14 wirelessly transmits the detailed data input from the emergency level determination unit 12 to the wireless communication terminal 20 through the antenna 15. Furthermore, the wireless communication unit 14 receives the measurement mode change signal serving as an instruction to change the operation mode of the IMD 10 from the emergency mode to the normal mode from the wireless communication terminal 20 through the antenna 15. The Power Down detection unit 16 receives the Power Down signal transmitted from the wireless communication terminal 20. Furthermore, when the Power Down signal has been received, the Power Down detection unit 16 outputs the received Power Down signal to the control unit 13.

Figure 3:
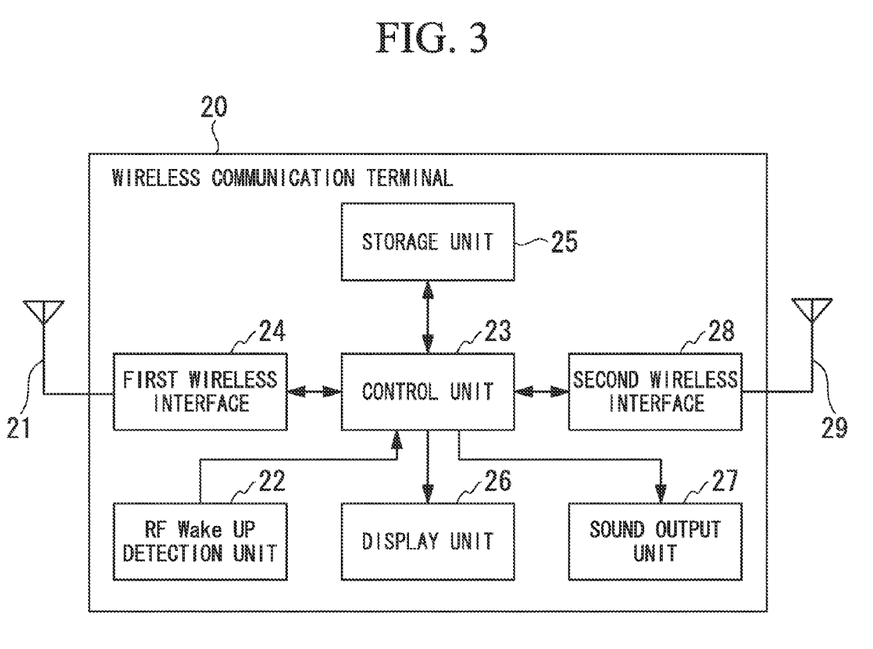
FIG. 3 is a block diagram illustrating the configuration of the wireless communication terminal in accordance with the first preferred embodiment of the present invention.

Next, the configuration of the wireless communication terminal 20 will be described. FIG. 3 is a block diagram illustrating the configuration of the wireless communication terminal 20 in accordance with the first preferred embodiment of the present invention. In the illustrated example, the wireless communication terminal 20 includes antennas 21 and 29, an RF Wake UP detection unit 22 (an activation signal reception unit), a control unit 23, a first wireless interface 24 (a wireless communication unit, a first wireless communication unit), a storage unit 25, a display unit 26, a sound output unit 27, and a second wireless interface 28 (a second communication unit).

The RF Wake UP detection unit 22 receives an RF Wake UP signal (an activation signal) transmitted from the IMD 10 through the antenna 21. Furthermore, when the RF Wake UP signal has been received, the RF Wake UP detection unit 22 outputs the received RF Wake UP signal to the control unit 23.

The control unit 23 controls the units provided in the wireless communication terminal 20. Furthermore, when the RF Wake UP signal has been input from the RF Wake UP detection unit 22, the control unit 23 activates the first wireless interface 24. Furthermore, based on the detailed data input from the first wireless interface 24, the control unit 23 determines whether an event detected by the IMD 10 is a mild event or a severe event. Furthermore, the control unit 23 controls the second wireless interface 28 to transmit the detailed data input from the first wireless interface 24 to the Web server 30. Furthermore, when a detailed determination signal transmitted from the Web server 30 indicates that the operation mode of the IMD 10 is changed from the emergency mode to the normal mode, the control unit 23 controls the first wireless interface 24 to transmit the data measurement mode change signal for instructing a change from the emergency mode to the normal mode to the IMD 10.

Furthermore, when the detailed determination signal transmitted from the Web server 30 indicates that the operation mode of the IMD 10 is changed from the emergency mode to the normal mode, the wireless communication terminal 20 controls the first wireless interface 24 to transmit the Power Down signal to the IMD 10, wherein the Power Down signal instructs to stop the operation of the wireless communication unit of the IMD 10.

Furthermore, the control unit 23 controls content based on the detailed data to be displayed on the display unit 26, and controls sound based on the detailed data to be output to the sound output unit 27. For example, when the acquired detailed data is emergency data, the control unit 23 controls display data (for example, alarm information indicating that help is needed, emergency information, the state of a patient, the condition of a patient, an emergency contact number (a home contact number or a hospital contact number) and the like) stored in the storage unit 25, an electrocardiogram based on the detailed data, and the like to be displayed on the display unit 26, and controls sound data (for example, a sound signal or an alarm sound indicating that help is needed, and the like)

stored in the storage unit 25 in advance to be periodically divided and output to the sound output unit 27.

If the first wireless interface 24 is activated by the control unit 23, the first wireless interface 24 receives the detailed data transmitted from the IMD 10 through the antenna 21, and outputs the received detailed data to the control unit 23. Furthermore, the first wireless interface 24 transmits the data measurement mode change signal and the Power Down signal to the IMD 10 under the control of the control unit 23.

The storage unit 25 stores the detailed data transmitted from the IMD 10. Furthermore, the storage unit 25 stores the display data and the sound data. The display unit 26 is a display device such as a liquid crystal display (LCD), and displays content corresponding to the detailed data under the control of the control unit 23. The sound output unit 27 is a speaker and the like, and outputs sound corresponding to the detailed data under the control of the control unit 23.

The second wireless interface 28 transmits the detailed data transmitted from the IMD 10 to the Web server 30 through the antenna 29 under the control of the control unit 23. Furthermore, the second wireless interface 28 receives the detailed determination signal transmitted from the Web server 30 through the antenna 29. Furthermore, the second wireless interface 28 outputs the received detailed determination signal to the control unit 23.

Figure 4:
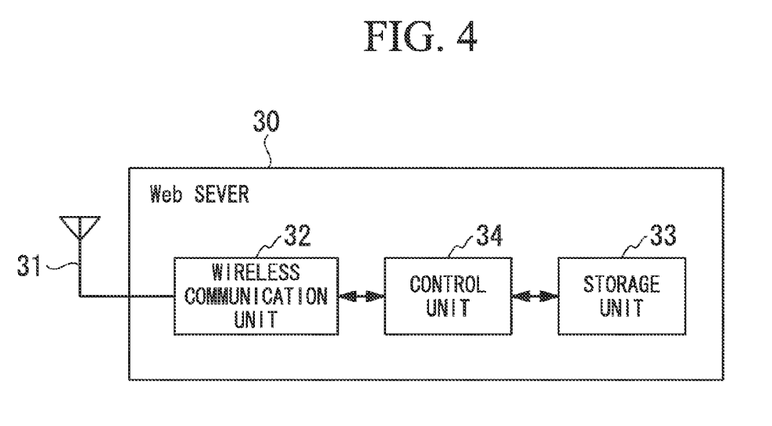
FIG. 4 is a block diagram illustrating the configuration of the Web server in accordance with the first preferred embodiment of the present invention.

Next, the configuration of the Web server 30 will be described. FIG. 4 is a block diagram illustrating the configuration of the Web server 30 in accordance with the first preferred embodiment of the present invention. In the example illustrated in FIG. 4, the Web server 30 includes an antenna 31, a wireless communication unit 32 (a communication unit), a storage unit 33, and a control unit 34 (a comparison unit, a server control unit).

The wireless communication unit 32 receives the detailed data transmitted from the wireless communication terminal 20 through the antenna 31. Furthermore, the wireless communication unit 32 outputs the received detailed data to the control unit 34. Furthermore, the wireless communication unit 32 transmits the detailed determination signal to the wireless communication terminal 20 through the antenna 31 under the control of the control unit 34.

The storage unit 33 stores an SDB (server data base) information data block (comparison vital data). The SDB information data block, for example, indicates heart rate data, blood sugar data and the like, and includes various types of data used when the control unit 34 detects the abnormality of the detailed data. The control unit 34 detects the abnormality of the detailed data using the SDB information data block stored in the storage unit 33 and the detailed data transmitted from the wireless communication terminal 20, and performs a detailed determination process of determining whether or not to change the operation mode of the IMD 10 from the emergency mode to the normal mode. Then, the control unit 34 controls the wireless communication unit 32 to transmit a detailed determination signal to the wireless communication terminal 20, wherein the detailed determination signal indicates a result of the detailed determination process. In addition, since the data amount of the SDB information data block stored in the storage unit 33 is enormous and the control unit 34 determines whether or not to change the operation mode of the IMD 10 from the emergency mode to the normal mode using the SDB information data block with the enormous data amount, it is possible for the control unit 34 to perform more accurate determination.

Figure 5:
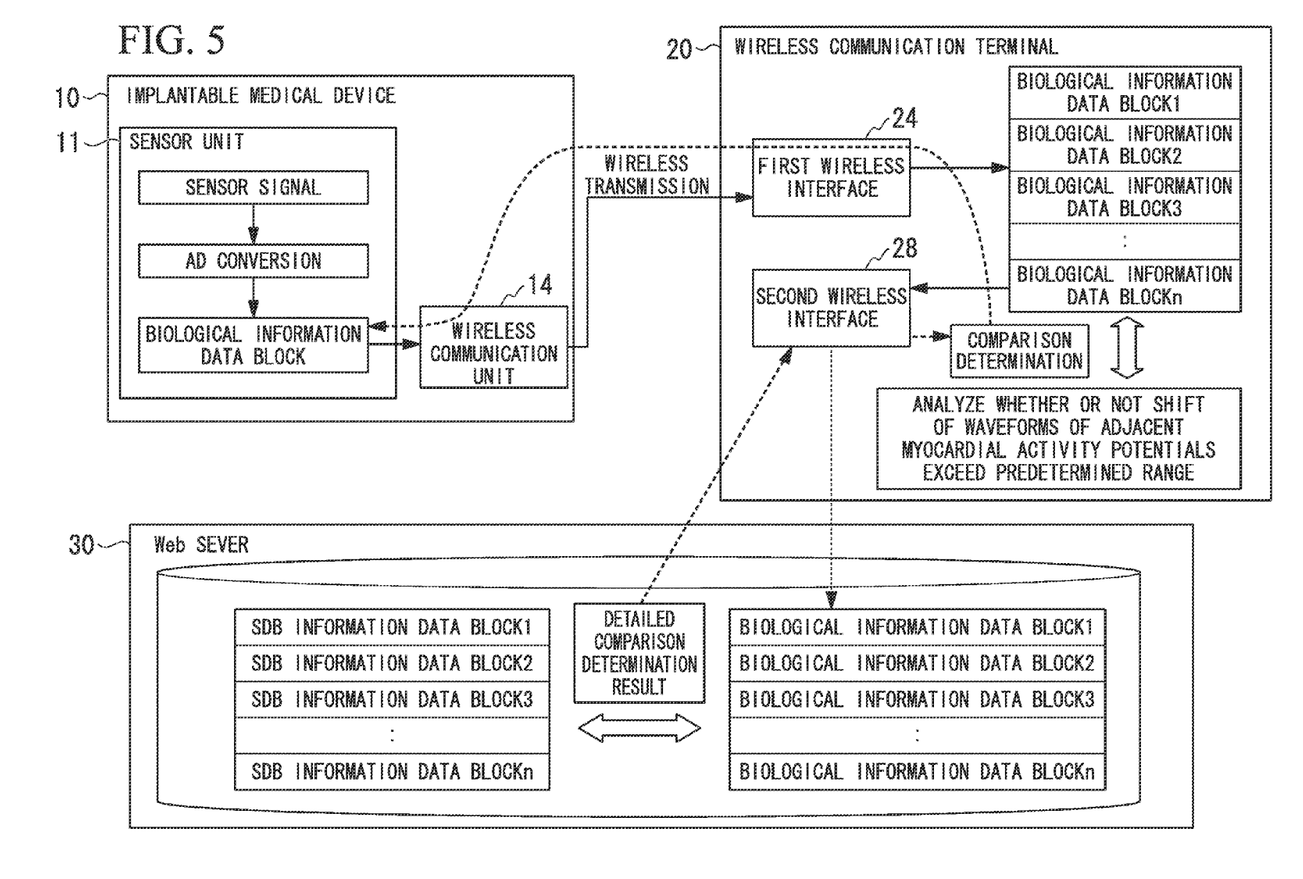
FIG. 5 is a schematic diagram illustrating data flow when the wireless communication terminal performs the schematic determination process and the Web server performs the detailed determination process in accordance with the first preferred embodiment of the present invention.

Next, the schematic determination process and the detailed determination process will be described. FIG. 5 is a schematic diagram illustrating data flow when the wireless communication terminal 20 performs the schematic determination process and the Web server 30 performs the detailed determination process in accordance with the first preferred embodiment of the present invention. In addition, according to the schematic determination process, it is determined whether or not to change the operation mode of the IMD 10 from the emergency mode to the normal mode using only the detailed data acquired by the IMD 10. Furthermore, according to the detailed determination process, it is determined whether or not to change the operation mode of the IMD 10 from the emergency mode to the normal mode using the detailed data acquired by the IMD 10 and the SDB information data block stored in the storage unit 33. In addition, a condition for a change from the emergency mode to the normal mode is established when the detailed data does not include abnormal data (when no abnormality is detected). Accordingly, it is determined not to change the operation mode from the emergency mode to the normal mode when the abnormality of the detailed data is detected, and it is determined to change the operation mode from the emergency mode to the normal mode when no abnormality of the detailed data is detected.

Hereinafter, a description will be provided for a method in which the control unit 23 of the wireless communication terminal 20 analyzes the detailed data at the time of execution of the schematic determination process, and detects the abnormality when the detailed data is a myocardial activity potential. As illustrated in FIG. 5, the sensor unit 11 of the IMD 10 performs AD conversion with respect to a myocardial activity potential acquired as an analog signal, collects a myocardial activity potential of a digital signal for a predetermined time period, and generates a biological information data block. Then, the wireless communication unit 14 of the IMD 10 transmits the biological information data block to the wireless communication terminal 20. The first wireless interface 24 of the wireless communication terminal 20 receives the biological information data block transmitted from the IMD 10, and outputs the biological information data block to the control unit 23. Furthermore, the control unit 23 detects abnormality based on the biological information data block input from the first wireless interface 24.

As a method of detecting the abnormality, for example, as disclosed in Japanese Unexamined Patent Application, First Publication No. 2009-247812, a method of detecting the abnormality when a shift of waveforms of adjacent myocardial activity potentials relative to a time axis continuously occurs during two or more cycles beyond a predetermined range, in order to perform prompt action when an abnormal myocardial activity potential has been generated, has been disclosed. In addition, since this method includes a cycle-based point-synchronizing algorithm which synchronizes an input myocardial activity potential with the same base point each cycle, and an overlap-displaying algorithm which simultaneously and overlappingly displays at least two cycles of waveforms of a myocardial activity potential which continues relative to a time axis, it is possible to easily detect a change in the waveforms. Furthermore, when the waveform of the myocardial activity potential has been changed beyond a predetermined range, since the method includes a wavelength-adjusting algorithm which adjusts the waveform of the myocardial activity potential after change to be the same as that of the myocardial activity potential before change, it is possible to prevent a shift of the waveform of the myocardial activity potential due to a change in the wavelength thereof from being misunderstood as an abnormal waveform.

Furthermore, in the schematic determination process, since the control unit 23 of the wireless communication terminal 20 controls the sound output unit 27 to issue an alarm when the shift of waveforms of adjacent myocardial activity potentials relative to the time axis has continuously occurred during two or more cycles beyond the predetermined range, there is no false alarm due to the generation of architecture (normally, the same waveform is not continuously generated during two or more cycles) caused by body movement and the like, and it is possible to issue an alarm only when an abnormal waveform has occurred. Furthermore, when the alarm has been issued as described above, it is possible for a user to promptly cope with the abnormality of the myocardial activity potential, and to quickly determine the abnormality of a cardiovascular function which causes the above abnormality.

Furthermore, the control unit 23 of the wireless communication terminal 20 controls the second wireless interface 28 to transmit the biological information data block transmitted from the IMD 10 to the Web server 30 through the antenna 29.

The control unit 34 of the Web server 30 compares the SDB information data block stored in the storage unit 33 with the biological information data block transmitted from the wireless communication terminal 20 to detect the abnormality of the biological information data block, and performs the detailed determination process of determining whether or not to change the operation mode of the IMD 10 from the emergency mode to the normal mode. Then, the control unit 34 controls the wireless communication unit 32 to transmit a detailed determination signal indicating a determination process result to the wireless communication terminal 20.

In addition, a method in which the control unit 34 of the Web server 30 analyzes the detailed data at the time of execution of the detailed determination process, and detects the abnormality, for example, has been disclosed in Japanese Unexamined Patent Application, First Publication No. 2008-119479. Specifically, in order to discriminate tachyarrhythmia, atrial and ventricular activities are monitored, tachyarrhythmia is checked in the monitored activities, a classification algorithm is operated to discriminate the tachyarrhythmia between ventricular tachycardia and supra-ventricular tachycardia according to predetermined criteria, and the release of a shock therapy defibrillation, cardioversion, and anti-tachycardia ventricular stimulation in the presence of ventricular tachycardia is permitted, and abnormality of detailed data is discriminated from waveform data of the heart for a predetermined time period.

Figure 6:
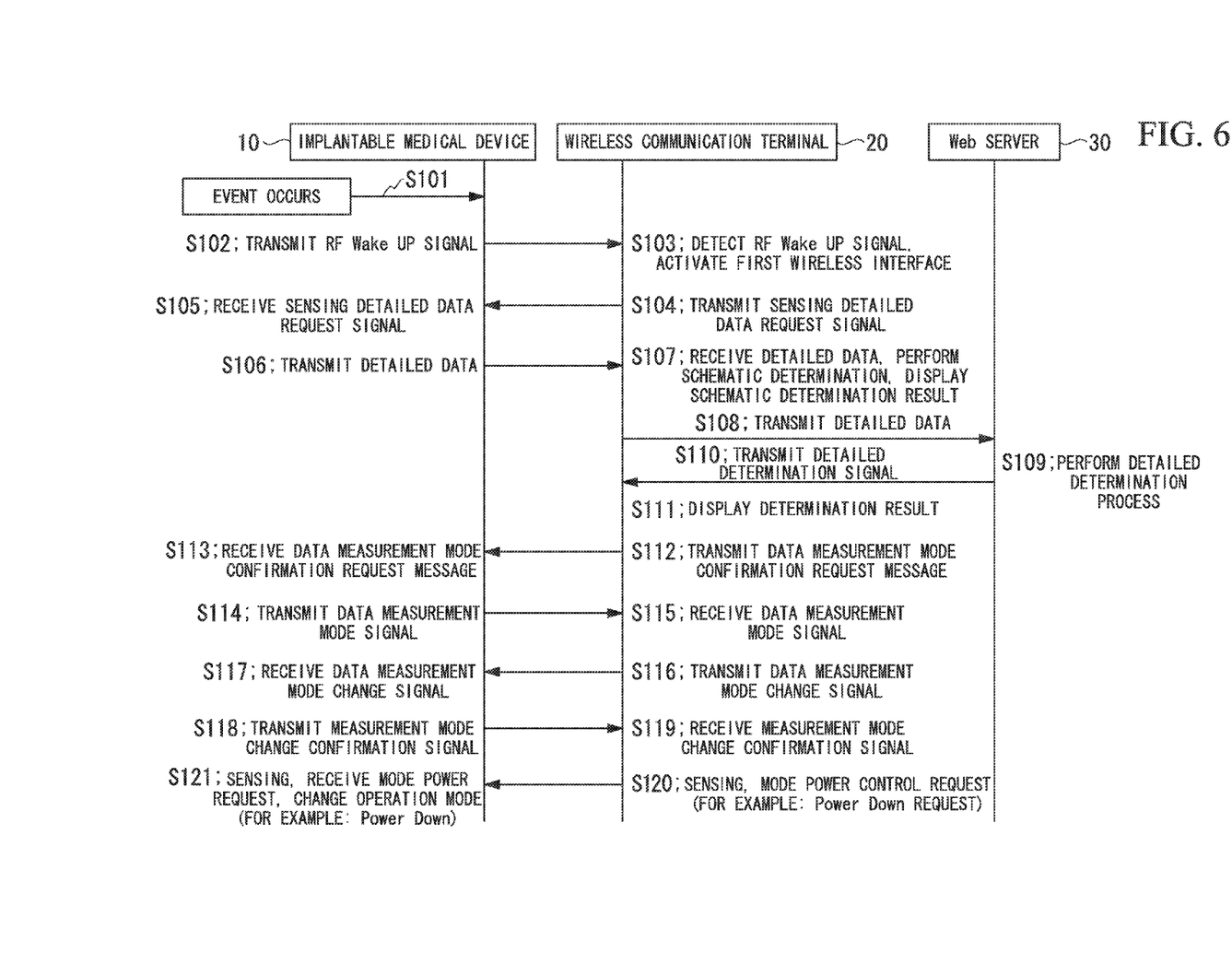
FIG. 6 is a sequence diagram illustrating the operation procedures of the IMD and the wireless communication terminal in accordance with the first preferred embodiment of the present invention.

Next, operation procedures of the IMD 10, the wireless communication terminal 20, and the Web server 30 in accordance with the first preferred embodiment of the present invention will be described. FIG. 6 is a sequence diagram illustrating the operation procedures of the IMD 10, the wireless communication terminal 20, and the Web server 30 in accordance with the first preferred embodiment of the present invention.

(Step S101)

The sensor unit 11 of the IMD 10 acquires the detailed data and outputs the acquired detailed data to the emergency level determination unit 12. The emergency level determination unit 12 detects an event based on the detailed data input from the sensor unit 11.

(Step S102)

When the event has been detected, the emergency level determination unit 12 determines whether or not to change the operation mode of the IMD 10 from the normal mode to the emergency mode. Then, when the emergency level determination unit 12 has determined to change the operation mode to the emergency mode, the control unit 13 changes the operation mode of the IMD 10 to the emergency mode, and activates the wireless communication unit 14. Thereafter, the control unit 13 controls the wireless communication unit 14 to transmit the RF Wake UP signal to the wireless communication terminal 20.

(Step S103)

The RF Wake UP detection unit 22 of the wireless communication terminal 20 receives the RF Wake UP signal transmitted from the IMD 10 through the antenna 21, and outputs the received RF Wake UP signal to the control unit 23. When the RF Wake UP signal has been input from the RF Wake UP detection unit 22, the control unit 23 activates the first wireless interface 24.

(Step S104)

The control unit 23 of the wireless communication terminal 20 controls the first wireless interface 24 to transmit a sensing detailed data request signal to the IMD 10.

(Step S105)

The wireless communication unit 14 of the IMD 10 receives the sensing detailed data request signal transmitted from the wireless communication terminal 20.

(Step S106)

When the wireless communication unit 14 has received the sensing detailed data request signal, the control unit 13 of the IMD 10 controls the wireless communication unit 14 to transmit the detailed data detected by the sensor unit 11 to the wireless communication terminal 20.

(Step S107)

The first wireless interface 24 of the wireless communication terminal 20 receives the detailed data transmitted from the IMD 10. Furthermore, the control unit 23 of the wireless communication terminal 20 performs schematic determination based on the detailed data received in the first wireless interface 24, and determines whether or not to change the operation mode of the IMD 10 from the emergency mode to the normal mode. Furthermore, the control unit 23 of the wireless communication terminal 20 controls a determination result of the schematic determination to be displayed on the display unit 26.

(Step S108)

The control unit 23 of the wireless communication terminal 20 controls the second wireless interface 28 to transmit the detailed data received from the IMD 10 to the Web server 30.

(Step S109)

The wireless communication unit 32 of the Web server 30 receives the detailed data transmitted from the wireless communication terminal 20. Furthermore, the control unit 34 of the Web server 30 detects the abnormality of the detailed data using the detailed data received in the wireless communication unit 32 and the SDB information data block stored in the storage unit 33, and performs the detailed determination process of determining whether or not to change the operation mode of the IMD 10 from the emergency mode to the normal mode.

(Step S110)

The control unit 34 of the Web server 30 controls the wireless communication unit 32 to transmit the detailed determination signal indicating the result of the detailed determination process to the wireless communication terminal 20.

(Step S111)

The second wireless interface 28 of the wireless communication terminal 20 receives the detailed determination signal transmitted from the Web server 30. Furthermore, based on the detailed determination signal, the control unit 23 of the wireless communication terminal 20 determines whether or not to change the operation mode of the IMD 10 from the emergency mode to the normal mode. Furthermore, the control unit 23 of the wireless communication terminal 20 controls the determination result indicated by the detailed determination signal to be displayed on the display unit 26.
(Step S112)
The control unit 23 of the wireless communication terminal 20 controls the first wireless interface 24 to transmit the data measurement mode confirmation request message to the IMD 10.
(Step S113)
The wireless communication unit 14 of the IMD 10 receives the data measurement mode confirmation request message transmitted from the wireless communication terminal 20.
(Step S114)
The control unit 13 of the IMD 10 controls the wireless communication unit 14 to transmit a data measurement mode signal indicating a current operation mode to the wireless communication terminal 20.
(Step S115)
The first wireless interface 24 of the wireless communication terminal 20 receives the data measurement mode signal transmitted from the IMD 10.
(Step S116)
When an operation mode specified by the data measurement mode signal received in step S115 is the emergency mode and the detailed determination signal received in the process of step S111 indicates that the operation mode of the IMD 10 is changed from the emergency mode to the normal mode, the control unit 23 of the wireless communication terminal 20 transmits the data measurement mode change signal to the IMD 10, wherein the data measurement mode change signal instructs a change in the operation mode of the IMD 10 from the emergency mode to the normal mode.
(Step S117)
The wireless communication unit 14 of the IMD 10 receives the data measurement mode change signal transmitted from the wireless communication terminal 20.
(Step S118)
When the wireless communication unit 14 has received the data measurement mode change signal, the control unit 13 of the IMD 10 changes the operation mode from the emergency mode to the normal mode, and performs a process corresponding to the normal mode. Furthermore, the control unit 13 controls the wireless communication unit 14 to transmit a measurement mode change confirmation signal to the wireless communication terminal 20, wherein the measurement mode change confirmation signal indicates that the operation mode has been changed to the normal mode.
(Step S119)
The first wireless interface 24 of the wireless communication terminal 20 receives the measurement mode change confirmation signal transmitted from the IMD 10.
(Step S120)
Since the operation mode of the IMD 10 has been changed to the normal mode, the control unit 23 of the wireless communication terminal 20 controls the first wireless interface 24 to transmit the Power Down signal to the IMD 10.
(Step S121)
The Power Down detection unit 16 of the IMD 10 receives the Power Down signal transmitted from the wireless communication terminal 20, and outputs the received Power Down signal to the control unit 13. When the Power Down signal has been input, the control unit 13 of the IMD 10 stops the operation of the wireless communication unit 14.

Figure 7:
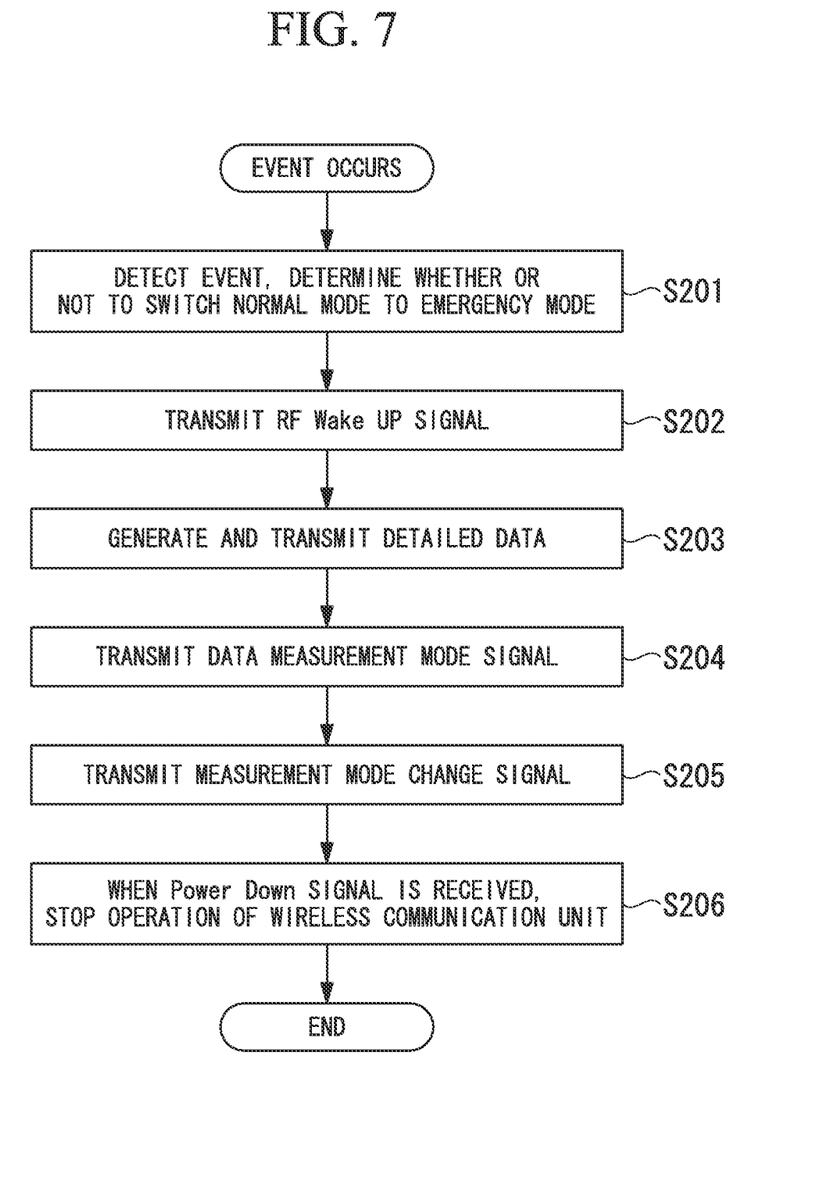
FIG. 7 is a flowchart illustrating the operation procedure of the IMD in accordance with the first preferred embodiment of the present invention.

Next, the operation procedure of the IMD 10 will be described. FIG. 7 is a flowchart illustrating the operation procedure of the IMD 10 in accordance with the first preferred embodiment of the present invention.
(Step S201)
The sensor unit 11 acquires the detailed data and outputs the acquired detailed data to the emergency level determination unit 12. The emergency level determination unit 12 detects an event based on the detailed data input from the sensor unit 11. Furthermore, when the event has been detected, the emergency level determination unit 12 determines whether or not to switch the operation mode of the IMD 10 from the normal mode to the emergency mode. Then, when the emergency level determination unit 12 has determined to switch the operation mode to the emergency mode, the control unit 13 switches the operation mode of the IMD 10 to the emergency mode, and activates the wireless communication unit 14. Thereafter, the control unit 13 proceeds to a process of step S202.
(Step S202)
The control unit 13 controls the wireless communication unit 14 to transmit the RF Wake UP signal to the wireless communication terminal 20. Thereafter, the control unit 13 proceeds to a process of step S203.
(Step S203)
When the wireless communication unit 14 has received the sensing detailed data request signal, the control unit 13 controls the wireless communication unit 14 to transmit the detailed data detected by the sensor unit 11 to the wireless communication terminal 20. Thereafter, the control unit 13 proceeds to a process of step S204.
(Step S204)
When the wireless communication unit 14 has received the data measurement mode confirmation request message, the control unit 13 controls the wireless communication unit 14 to transmit the data measurement mode signal indicating a current data measurement mode state to the wireless communication terminal 20. Thereafter, the control unit 13 proceeds to a process of step S205.
(Step S205)
When the wireless communication unit 14 has received the data measurement mode change signal, the control unit 13 changes the operation mode from the emergency mode to the normal mode, and performs a process corresponding to the normal mode. Furthermore, the control unit 13 controls the wireless communication unit 14 to transmit the measurement mode change confirmation signal to the wireless communication terminal 20, wherein the measurement mode change confirmation signal indicates that the operation mode has been changed to the normal mode. Thereafter, the control unit 13 proceeds to a process of step S206.
(Step S206)
When the Power Down detection unit 16 has received the Power Down signal, the control unit 13 stops the operation of the wireless communication unit 14. Thereafter, the operation procedure is ended.

Figure 8:
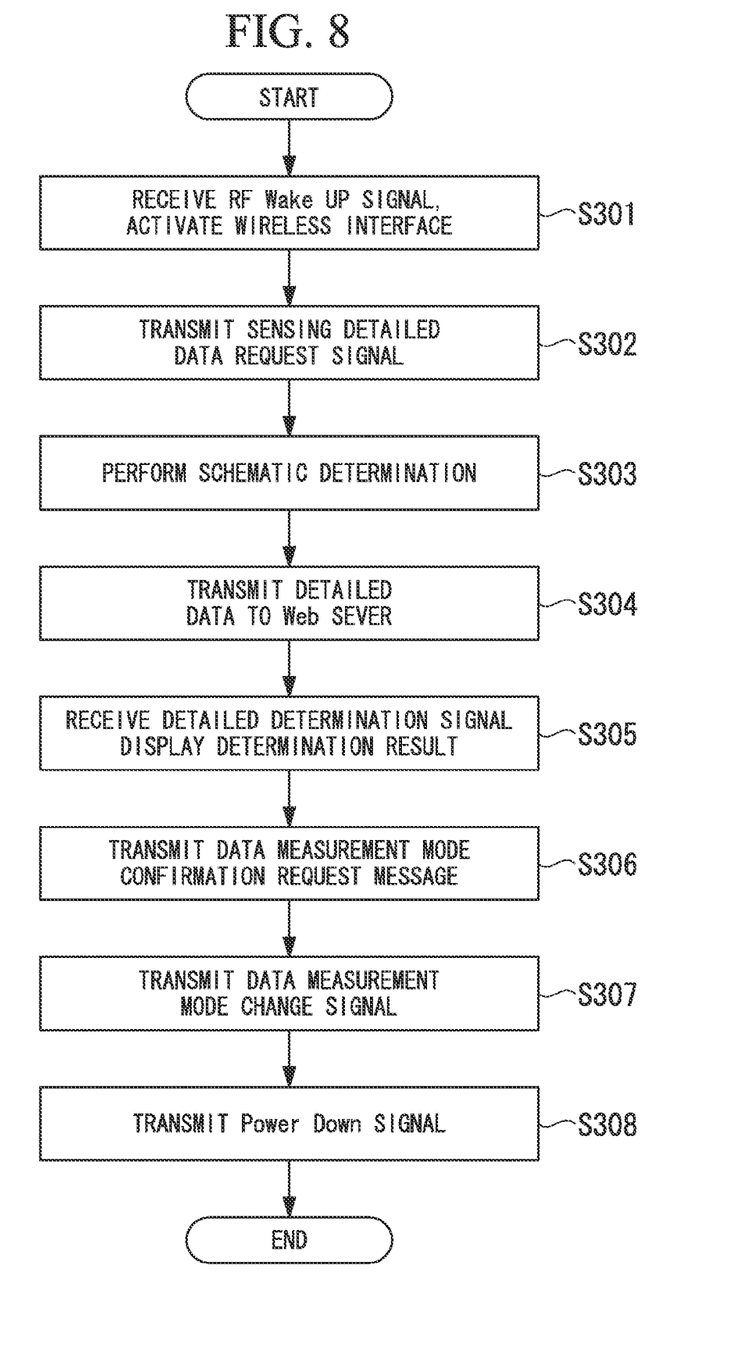
FIG. 8 is a flowchart illustrating the operation procedure of the wireless communication terminal in accordance with the first preferred embodiment of the present invention.

Next, the operation procedure of the wireless communication terminal 20 will be described. FIG. 8 is a flowchart illustrating the operation procedure of the wireless communication terminal 20 in accordance with the first preferred embodiment of the present invention.
(Step S301)
When the RF Wake UP detection unit 22 has received the RF Wake UP signal, the control unit 23 activates the first wireless interface 24. Thereafter, the control unit 23 proceeds to a process of step S302.
(Step S302)
The control unit 23 controls the first wireless interface 24 to transmit the sensing detailed data request signal to the IMD 10. Thereafter, the control unit 23 proceeds to a process of step S303.

(Step S303)

When the first wireless interface 24 has received the detailed data, the control unit 23 performs the schematic determination based on the detailed data, and determines whether or not to change the operation mode of the IMD 10 from the emergency mode to the normal mode. Furthermore, the control unit 23 controls a determination result of the schematic determination to be displayed on the display unit 26. Thereafter, the control unit 23 proceeds to a process of step S304.

(Step S304)

The control unit 23 controls the second wireless interface 28 to transmit the detailed data received from the IMD 10 to the Web server 30. Thereafter, the control unit 23 proceeds to a process of step S305.

(Step S305)

When the second wireless interface 28 has received the detailed determination signal, the control unit 23 determines whether or not the received detailed determination signal indicates a change in the operation mode of the IMD 10 from the emergency mode to the normal mode. Furthermore, the control unit 23 controls a determination result indicated by the detailed determination signal to be displayed on the display unit 26. Thereafter, the control unit 23 proceeds to a process of step S306.

(Step S306)

The control unit 23 controls the first wireless interface 24 to transmit the data measurement mode confirmation request message to the IMD 10. Thereafter, the control unit 23 proceeds to a process of step S307.

(Step S307)

When the first wireless interface 24 has received the data measurement mode signal, if an operation mode specified by the received data measurement mode signal is the emergency mode and the detailed determination signal received in the process of step S305 indicates that the operation mode of the IMD 10 is changed from the emergency mode to the normal mode, the control unit 23 transmits the data measurement mode change signal to the IMD 10, wherein the data measurement mode change signal instructs a change in the operation mode of the IMD 10 from the emergency mode to the normal mode. Thereafter, the control unit 23 proceeds to a process of step S308.

(Step S308)

When the first wireless interface 24 has received the measurement mode change confirmation signal, the control unit 23 controls the first wireless interface 24 to transmit the Power Down signal to the IMD 10. Thereafter, the operation procedure is ended.

Figure 9:
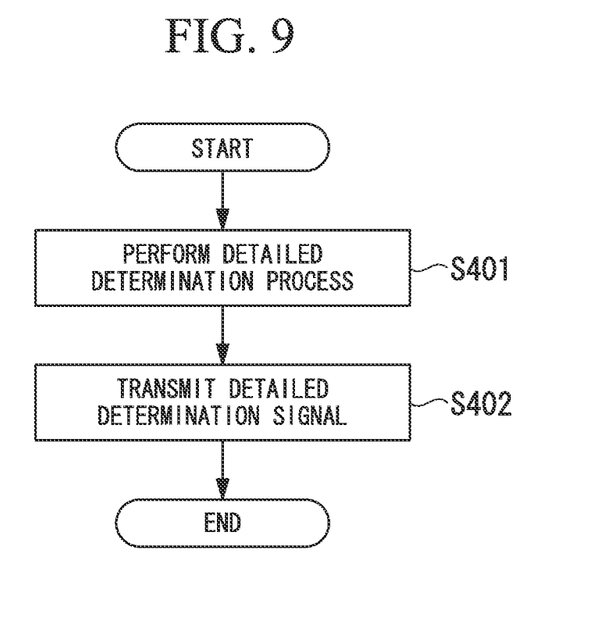
FIG. 9 is a flowchart illustrating the operation procedure of the Web server in accordance with the first preferred embodiment of the present invention.

Next, the operation procedure of the Web server 30 will be described. FIG. 9 is a flowchart illustrating the operation procedure of the Web server 30 in accordance with the first preferred embodiment of the present invention.

(Step S401)

When the wireless communication unit 32 has received the detailed data, the control unit 34 detects the abnormality of the detailed data using the received detailed data and the SDB information data block stored in the storage unit 33, and performs the detailed determination process of determining whether or not to change the operation mode of the IMD 10 from the emergency mode to the normal mode. Thereafter, the control unit 34 proceeds to a process of step S402.

(Step S402)

The control unit 34 controls the wireless communication unit 32 to transmit a detailed determination signal to the wireless communication terminal 20, wherein the detailed determination signal indicates a determination result in the process of step S401. Thereafter, the operation procedure is ended.

As described above, according to the first preferred embodiment of the present invention, the Web server 30 stores the SDB information data block used in order to detect the abnormality of the detailed data acquired by the IMD 10. Then, the Web server 30 detects the abnormality of the detailed data using the stored SDB information data block and the detailed data transmitted from the wireless communication terminal 20, and performs the detailed determination process of determining whether or not to change the operation mode of the IMD 10 from the emergency mode to the normal mode. Accordingly, it is possible for the Web server 30 to more accurately detect the abnormality of the detailed data acquired by the IMD 10.

Furthermore, according to the first preferred embodiment of the present invention, the IMD 10 operates in one of two modes, that is, the normal mode in which a data acquisition interval is long, or the emergency mode in which the data acquisition interval is short. Determination of switching from the normal mode to the emergency mode is performed by the IMD 10. Thus, for example, when the IMD 10 has detected an emergency event, since the IMD 10 performs the determination of the switching from the normal mode to the emergency mode, it is possible to switch the operation mode to the emergency mode more quickly, as compared with the case in which the wireless communication terminal 20 or the Web server 30 performs the determination of the switching from the normal mode to the emergency mode.

Furthermore, according to the first preferred embodiment of the present invention, determination of switching of the operation mode of the IMD 10 from the emergency mode to the normal mode is performed by the wireless communication terminal 20 or the Web server 30. Thus, since the IMD 10 does not need to perform the determination of the switching from the emergency mode to the normal mode, it is possible to further reduce the consumption of a battery provided in the IMD 10. Moreover, since it is possible to more accurately detect the abnormality of the detailed data, it is also possible for the Web server 30 to more accurately determine whether or not to change the operation mode of the IMD 10 from the emergency mode to the normal mode.

Furthermore, according to the first preferred embodiment of the present invention, when the operation mode of the IMD 10 is switched from the emergency mode to the normal mode, the wireless communication terminal 20 transmits the Power Down signal to the IMD 10. Furthermore, when the Power Down signal has been received, the IMD 10 stops the operation of the wireless communication unit 14. Thus, when the detailed data is not transmitted to the wireless communication terminal 20, it is possible for the IMD 10 to stop the wireless communication unit 14, so that it is possible to further reduce the consumption of the battery provided in the IMD 10.

While preferred embodiments of the present invention have been described and illustrated above, it should be understood that these are examples of the present invention and are not to be considered as limiting. Additions, omissions, substitutions, and other modifications can be made without departing from the scope of the present invention.

For example, the IMD 10 and the wireless communication terminal 20 in accordance with the above-mentioned first preferred embodiment of the present invention wirelessly communicate with each other in a one-to-one manner. However, the present invention is not limited thereto. For example, the IMD 10 and the wireless communication terminal 20 may wirelessly communicate with each other in a multi-to-multi manner. Furthermore, the wireless communication terminal 20 and the Web server 30 wirelessly communicate with each other in a one-to-one manner. However, the present invention is not limited thereto. For example, the wireless communication terminal 20 and the Web server 30 may wirelessly communicate with each other in a multi-to-multi manner. Furthermore, communication between the wireless communication terminal 20 and the Web server 30 may include wired communication.

Furthermore, according to the first preferred embodiment of the present invention, the Web server 30 detects the abnormality of the detailed data using the detailed data acquired by the IMD 10 and the SDB information data block stored in the storage unit 33, and performs the detailed determination process of determining whether or not to change the operation mode of the IMD 10 from the emergency mode to the normal mode. However, the present invention is not limited thereto. For example, the wireless communication terminal 20 may receive the SDB information data block from the Web server 30, detect the abnormality of the detailed data using the detailed data acquired by the IMD 10 and the SDB information data block received from the Web server 30, and perform the detailed determination process of determining whether or not to change the operation mode of the IMD 10 from the emergency mode to the normal mode.

Accordingly, the present invention is not to be considered as being limited by the foregoing description, and is only limited by the scope of the claims.

What is claimed is:

1. A wireless communication system comprising:
   a wireless communication interface configured to wirelessly receive vital data from a sensing terminal;
   a memory configured to store comparison vital data;
   a processor configured to compare the wirelessly received vital data with the comparison vital data and control the wireless communication interface to transmit an instruction for stopping wireless transmission of the vital data to the sensing terminal that has wirelessly transmitted the vital data, when no abnormality is detected in the vital data based on a comparison result of the processor; and
   an RF interface configured to receive an activation signal from the sensing terminal,
   wherein, when the RF interface receives the activation signal from the sensing terminal, the processor activates the wireless communication interface.

2. The wireless communication system according to claim 1, wherein the memory stores heart rate data or blood sugar data as the comparison vital data.

3. The wireless communication system according to claim 2, wherein the processor controls the wireless communication interface to transmit the instruction based on the result obtained by comparing the wirelessly received vital data with the comparison vital data for a plurality of cycles.

4. The wireless communication system according to claim 1, wherein, when, comparing two of a plurality of sensing modes of the sensing terminal, a mode having a relatively long sensing interval is defined as a first mode and a mode having a relatively short sensing interval is defined as a second mode, the instruction includes an instruction for operating the sensing terminal in the first mode.

5. The wireless communication system according to claim 1, wherein the processor controls the wireless communication interface to transmit an instruction for stopping an operation of the wireless communication interface in the sensing terminal that has wirelessly transmitted the vital data.

6. A wireless communication system comprising:
   a server; and
   a wireless communication terminal,
   wherein the server comprises:
   a wireless interface configured to communicate with the wireless communication terminal;
   a memory configured to store comparison vital data;
   a first processor configured to compare vital data received from the wireless communication terminal with the comparison vital data and control the wireless interface to transmit a comparison result signal indicating a comparison result of the first processor to the wireless communication terminal, and
   wherein the wireless communication terminal comprises:
   a first wireless communication interface configured to wirelessly receive the vital data from a sensing terminal;
   a second communication interface configured to transmit the vital data received from the sensing terminal to the server;
   a second processor configured to control the first wireless communication interface to transmit an instruction for stopping wireless transmission of the vital data to the sensing terminal that has wirelessly transmitted the vital data, when no abnormality is detected in the vital data based on the comparison result signal received from the server; and
   an RF interface configured to receive an activation signal from the sensing terminal,
   wherein, when the RF interface receives the activation signal from the sensing terminal, the second processor activates the first wireless communication interface.

7. A wireless communication method comprising:
   wirelessly receiving vital data from a sensing terminal;
   storing comparison vital data;
   comparing the wirelessly received vital data with the comparison vital data;
   controlling the wireless communication step to transmit an instruction for stopping wireless transmission of the vital data to the sensing terminal that has wirelessly transmitted the vital data, when no abnormality is detected in the vital data based on a comparison result in the comparing; and
   receiving an activation signal from the sensing terminal,
   wherein, when the activation signal is received from the sensing terminal, the wirelessly receiving step is activated.

* * * * *